(12) United States Patent
Umekawa

(10) Patent No.: US 12,102,468 B2
(45) Date of Patent: Oct. 1, 2024

(54) RADIATION IMAGING APPARATUS, RADIATION IMAGING SYSTEM, CONTROL METHOD OF RADIATION IMAGING APPARATUS, AND NON-TRANSITORY COMPUTER-READABLE STORAGE MEDIUM

(71) Applicant: CANON KABUSHIKI KAISHA, Tokyo (JP)

(72) Inventor: Kazuaki Umekawa, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 361 days.

(21) Appl. No.: 17/648,318

(22) Filed: Jan. 19, 2022

(65) Prior Publication Data

US 2022/0257207 A1 Aug. 18, 2022

(30) Foreign Application Priority Data

Feb. 12, 2021 (JP) .................................. 2021-021062

(51) Int. Cl.
*A61B 6/00* (2024.01)
*A61B 6/42* (2024.01)
(Continued)

(52) U.S. Cl.
CPC .......... *A61B 6/5258* (2013.01); *A61B 6/4233* (2013.01); *A61B 6/463* (2013.01);
(Continued)

(58) Field of Classification Search
CPC ..... A61B 6/4233; A61B 6/463; A61B 6/5258; A61B 6/54; A61B 6/56; A61B 6/582
See application file for complete search history.

(56) References Cited

U.S. PATENT DOCUMENTS 10,201,323 B2 * 2/2019 Tanaka .................. A61B 6/465
10,498,975 B2 * 12/2019 Tezuka .................. H04N 25/63
(Continued)

FOREIGN PATENT DOCUMENTS

JP 2014-28033 A 2/2014
JP 2014028033 A * 2/2014 ............... A61B 6/00

OTHER PUBLICATIONS

Translation of JP-2014028033 (Year: 2014).*
U.S. Appl. No. 17/649,433, Satoshi Kamei, filed Jan. 31, 2022.

*Primary Examiner* — Dani Fox
*Assistant Examiner* — Soorena Kefayati
(74) *Attorney, Agent, or Firm* — VENABLE LLP

(57) ABSTRACT

A radiation imaging apparatus comprising a detection unit in which a plurality of pixels are arranged, a communication unit configured to receive a control signal including an imaging mode for acquiring a radiation image by the detection unit and a controller is provided. The controller operates the detection unit in an imaging mode corresponding to the control signal if an imaging instruction is received in a first state in which a state of communication is normal, operates the detection unit in an abnormal imaging mode set in advance if the imaging instruction is received in a second state in which the state of communication is not normal, and operates the detection unit so as to acquire offset image data for an imaging mode different from the abnormal imaging mode while radiation irradiation is not performed in the second state.

15 Claims, 4 Drawing Sheets

(51) Int. Cl.
*A61B 6/46* (2024.01)
*G01N 23/04* (2018.01)

(52) U.S. Cl.
CPC ............... *A61B 6/54* (2013.01); *A61B 6/56* (2013.01); *G01N 23/04* (2013.01); *G01N 2223/303* (2013.01)

(56) References Cited

U.S. PATENT DOCUMENTS

| | | | |
|---|---|---|---|
| 10,856,834 B2* | 12/2020 | Uchiyama | H04N 23/30 |
| 2014/0295767 A1* | 10/2014 | Iijima | A61B 6/4283 |
| | | | 455/41.3 |
| 2016/0228087 A1* | 8/2016 | Oda | A61B 6/5211 |
| 2017/0272670 A1* | 9/2017 | Tezuka | H04N 25/63 |
| 2017/0332987 A1* | 11/2017 | Nonaka | A61B 6/5258 |
| 2018/0021004 A1* | 1/2018 | Ishii | A61B 6/54 |
| | | | 378/62 |
| 2019/0247003 A1* | 8/2019 | Uchiyama | H04N 5/32 |
| 2019/0282196 A1* | 9/2019 | Tezuka | G01T 1/175 |

\* cited by examiner

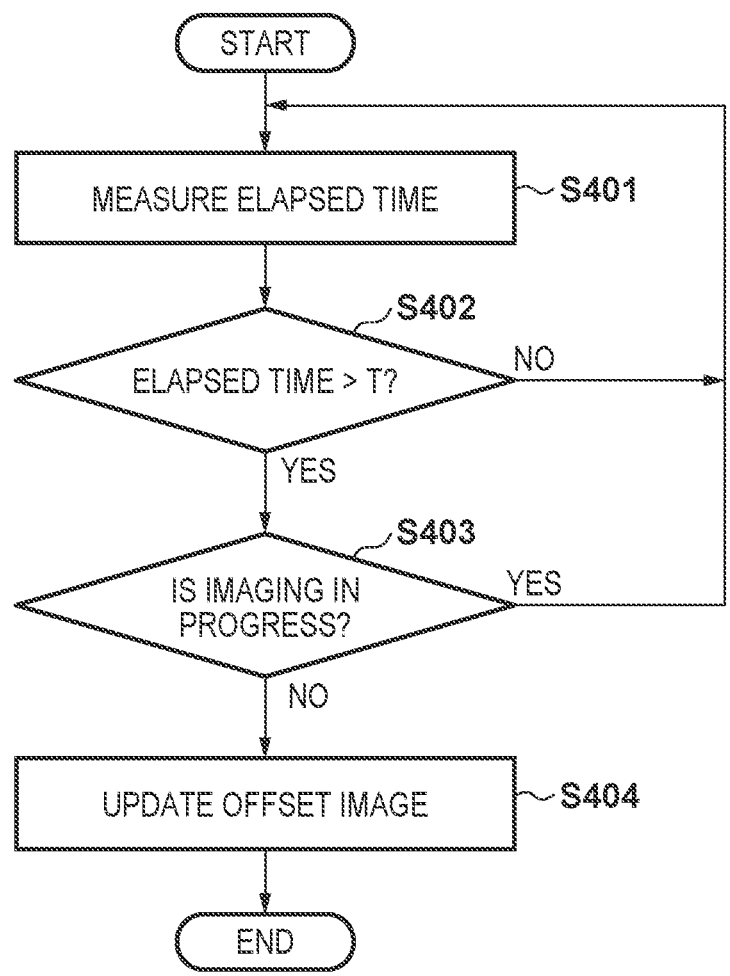

RADIATION IMAGING APPARATUS, RADIATION IMAGING SYSTEM, CONTROL METHOD OF RADIATION IMAGING APPARATUS, AND NON-TRANSITORY COMPUTER-READABLE STORAGE MEDIUM

BACKGROUND OF THE INVENTION

Field of the Invention

The present invention relates to a radiation imaging apparatus, a radiation imaging system, a control method of the radiation imaging apparatus, and a non-transitory computer-readable storage medium.

Description of the Related Art

In medical image diagnosis and nondestructive inspection, a radiation imaging apparatus using an FPD (Flat Panel Detector) made of a semiconductor material is widely used. Japanese Patent Laid-Open No. 2014-028033 describes a radiation imaging system in which the imaging mode of a radiation imaging apparatus is set by command communication from a command communication control apparatus in accordance with a user instruction. The radiation imaging system described in Japanese Patent Laid-Open No. 2014-028033 has an emergency imaging mode in which, even if the command communication control apparatus is down and command communication cannot be performed, the system operates in a specific imaging mode set in advance in accordance with a press of an emergency imaging transition button by a user or the like.

SUMMARY OF THE INVENTION

In a signal output from a pixel upon capturing a radiation image, not only a component corresponding to the applied radiation but also an offset component caused by the dark current of the pixel or the like exit. Therefore, offset correction is performed using offset image data acquired in a state in which no radiation is applied. The offset amount regarding the offset component changes in accordance with the imaging mode including the sensitivity setting, the accumulation time, the binning number, and the like for capturing the radiation image. Further, the offset amount regarding the offset component changes in accordance with a temperature change occurring along with an operation of the radiation imaging apparatus or the like. Accordingly, it is required to reacquire an offset image corresponding to each imaging mode at an appropriate timing. In the radiation imaging system described in Japanese Patent Laid-Open No. 2014-028033, when the command communication control apparatus is restored from the down status and imaging is to be performed after transition from the emergency imaging mode to a desired imaging mode, it is necessary to reacquire an offset image, and this may take a long time until the imaging is started.

Each of some embodiments of the present invention provides a technique advantageous in suppressing a waiting time in a radiation imaging apparatus.

According to some embodiments, a radiation imaging apparatus comprising: a detection unit in which a plurality of pixels used to acquire a radiation image corresponding to incident radiation are arranged; a communication unit configured to receive, from a control apparatus, a control signal including an imaging mode for acquiring the radiation image by the detection unit; and a controller, wherein the controller is configured to operate the detection unit in an imaging mode corresponding to the control signal if an imaging instruction is received in a first state in which a state of communication between the communication unit and the control apparatus is normal, operate the detection unit in an abnormal imaging mode set in advance if the imaging instruction is received in a second state in which the state of communication is not normal, and operate the detection unit so as to acquire offset image data for an imaging mode different from the abnormal imaging mode while radiation irradiation is not performed in the second state, is provided.

According to some other embodiments, a control method of a radiation imaging apparatus that comprises a detection unit in which a plurality of pixels used to acquire a radiation image corresponding to incident radiation are arranged, and a communication unit configured to communicate, with a control apparatus, a control signal including an imaging mode of acquiring the radiation image by the detection unit, the method comprising: determining whether a state of communication between the communication unit and the control apparatus is normal; operating the detection unit in an imaging mode corresponding to the control signal if an imaging instruction is received in a first state in which the state of communication is normal; and operating the detection unit in an abnormal imaging mode set in advance if an imaging instruction is received in a second state in which the state of communication is not normal, wherein the detection unit is operated so as to acquire offset image data for an imaging mode different from the abnormal imaging mode while radiation irradiation is not performed in the second state, is provided.

According to still other embodiments, a non-transitory computer-readable storage medium storing a program for causing a computer to execute a control method of a radiation imaging apparatus that comprises a detection unit in which a plurality of pixels used to acquire a radiation image corresponding to incident radiation are arranged, and a communication unit configured to communicate, with a control apparatus, a control signal including an imaging mode of acquiring the radiation image by the detection unit, the method comprising: determining whether a state of communication between the communication unit and the control apparatus is normal; operating the detection unit in an imaging mode corresponding to the control signal if an imaging instruction is received in a first state in which the state of communication is normal; and operating the detection unit in an abnormal imaging mode set in advance if an imaging instruction is received in a second state in which the state of communication is not normal, wherein the detection unit is operated so as to acquire offset image data for an imaging mode different from the abnormal imaging mode while radiation irradiation is not performed in the second state, is provided.

Further features of the present invention will become apparent from the following description of exemplary embodiments (with reference to the attached drawings).

BRIEF DESCRIPTION OF THE DRAWINGS

FIG. 4 is a flowchart for explaining another operation of the radiation imaging apparatus shown in FIG. 1.

DESCRIPTION OF THE EMBODIMENTS

Figure 1:
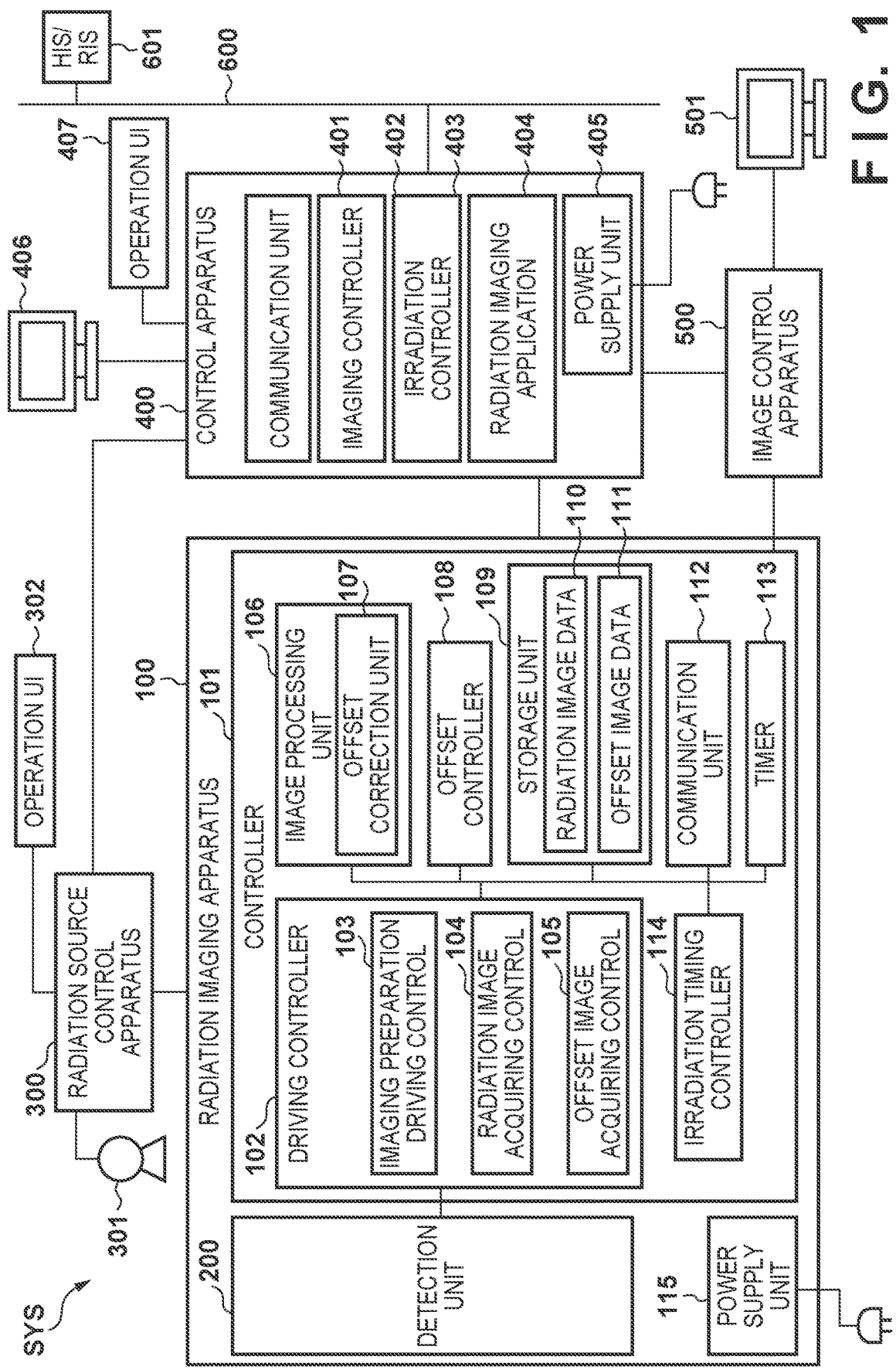
FIG. 1 is a block diagram showing a configuration example of a radiation imaging apparatus and a radiation imaging system using the radiation imaging apparatus according to an embodiment.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

Radiation in the present invention can include α-rays, β-rays, γ-rays, and the like which are beams generated by particles (including photons) emitted by radiation decay, as well as beams having the similar or higher energy, for example, X-rays, particle beams, cosmic rays, and the like.

With reference to FIGS. 1 to 4, the arrangement and operation of a radiation imaging apparatus according to this embodiment will be described. FIG. 1 is a block diagram showing an arrangement example of a radiation imaging apparatus 100 according to this embodiment. FIG. 1 also shows a block diagram of a radiation imaging system SYS using the radiation imaging apparatus 100 according to this embodiment. The radiation imaging apparatus 100 according to this embodiment can be used for, for example, medical purposes.

The radiation imaging system SYS includes the radiation imaging apparatus 100, a control apparatus 400, and a radiation source 301. The radiation imaging apparatus 100 includes a detection unit 200 in which a plurality of pixels used to acquire a radiation image corresponding to incident radiation are arranged. The radiation source 301 is controlled by a radiation source control apparatus 300, and irradiates the radiation imaging apparatus 100 with radiation. The control apparatus 400 controls the radiation imaging apparatus 100 and the radiation source control apparatus 300. The control apparatus 400 communicates control signals with the radiation imaging apparatus 100 to collect radiation image data from the radiation imaging apparatus 100 and display a radiation image based on the radiation image data. Further, the control apparatus 400 includes a radiation imaging application 404 that can accept an imaging order and register imaging information for generating a control signal including the imaging mode for acquiring a radiation image by the detection unit 200. The radiation imaging system SYS can further include an image control apparatus 500 that outputs, to the control apparatus 400, the radiation image data output from the radiation imaging apparatus 100.

The control apparatus 400 is connected to an in-hospital network 600 formed by, for example, a LAN (Local Area Network). An HIS (Hospital Information System)/RIS (Radiology Information System) 601 is connected to the in-hospital network 600. The control apparatus 400 and the HIS/RIS 601 can communicate with each other and exchange, for example, the imaging order of a radiation image, imaging information including patient information, and radiation image data in the hospital.

The radiation imaging apparatus 100 includes the detection unit 200, a controller 101, and a power supply unit 115. The detection unit detects the radiation entering the detection unit 200, and generates image data corresponding to the dose of the detected radiation. The controller 101 controls respective components arranged in the radiation imaging apparatus 100. The controller 101 includes a driving controller 102, an image processing unit 106, an offset controller 108, a storage unit 109, a communication unit 112, a timer 113, and an irradiation timing controller 114. The driving controller 102 controls the operation of the detection unit 200 so as to acquire radiation image data corresponding to radiation irradiation and offset image data used to correct the radiation image data. The image processing unit 106 performs image processing on image data acquired from the detection unit 200. The offset controller 108 controls the timing of updating an offset image. The storage unit 109 stores acquired image data. The communication unit 112 controls the communication with the control apparatus 400 and the communication with the radiation source control apparatus 300. For example, the communication unit 112 receives, from the control apparatus 400, a control signal including the imaging mode for acquiring a radiation image by the detection unit 200. The timer 113 acquires an imaging time, an elapse time, and the like. The irradiation timing controller 114 controls transition to the imaging operation of the detection unit 200 in accordance with a radiation irradiation signal from the radiation source control apparatus 300 to the radiation source 301. The power supply unit 115 supplies power to the respective components in the radiation imaging apparatus 100.

For example, the controller 101 may read out a program stored in the storage unit 109 and control the entire radiation imaging apparatus 100 based on the readout program. Further, the controller 101 may include a control signal generation circuit such as an ASIC and control the radiation imaging apparatus 100. Furthermore, control of the entire radiation imaging apparatus 100 may be implemented by both the program and the control signal generation circuit.

The driving controller 102 controls the detection unit 200 by switching a plurality of control modes including imaging preparation driving control 103, radiation image acquiring control 104, and offset image acquiring control 105. The imaging preparation driving control 103 is control for preparing the detection unit 200 in a state in which a radiation image can be captured. The radiation image acquiring control 104 is control for driving the detection unit 200 so as to acquire radiation image data. The offset image acquiring control 105 is control for driving the detection unit 200 so as to acquire offset image data. In the imaging preparation driving control 103, the driving controller 102 causes the detection unit 200 to periodically read out electric charges while applying a voltage similar to that upon imaging, so that dark charges accumulated in the respective pixels arranged in the detection unit 200 are reset. The signal read out from the pixel at this time is not handled as image data so may not be stored in the storage unit 109. In the radiation image acquiring control 104, the driving controller 102 drives the detection unit 200 as in the imaging preparation driving control 103, so that electric charges corresponding to radiation irradiation are accumulated in the pixels arranged in the detection unit 200. Then, the electric charges accumulated in the pixels are read out as radiation image data 110 and stored in the storage unit 109. A moving image can be captured by the driving controller 102 sequentially performing the radiation image acquiring control 104. In the offset image acquiring control 105, the driving controller 102 drives the detection unit 200 as in the imaging preparation driving control 103, and stores image data, which is read out in a state in which no radiation irradiation is performed, as offset image data 111 in the storage unit 109.

On the radiation image data 110 acquired from the detection unit 200 by the radiation image acquiring control 104, offset correction is performed using the offset image data 111 acquired in advance by the offset image acquiring control 105. The processing of offset correction may be performed by an offset correction unit 107 of the image processing unit 106. The radiation image data having undergone the offset correction is transferred to the image control apparatus 500 via the communication unit 112. Although only the processing of offset correction is described here, the image processing unit 106 may perform another correction processing such as defective pixel correction or gain correction of correcting the gain variation of the amplifier arranged in the detection unit 200. Alternatively, the correction processing as described above may not be performed in the radiation imaging apparatus 100. For example, the acquired radiation image data 110 and offset image data 111 may be transferred to the image control apparatus 500 without undergoing the correction processing or the like, and the image control apparatus 500 may perform the correction processing as described above. As the offset image data used for offset correction, for example, image data generated by acquiring a plurality of offset image data and performing noise component reduction processing by averaging or the like may be used.

The radiation source control apparatus 300 includes an operation UI 302 used to operate the radiation source control apparatus 300. The operation UI 302 can include a keyboard, a mouse, an exposure switch, and the like. A user may set a radiation irradiation condition or perform radiation irradiation using the operation UI 302. The radiation source control apparatus 300 and the radiation imaging apparatus 100 can exchange information using a dedicated signal line. The radiation source control apparatus 300 and the radiation imaging apparatus 100 may exchange, for example, synchronization signals such as a notification of the start or end of radiation irradiation and a notification of the radiation irradiation enable timing. With this, the radiation imaging apparatus 100 and the radiation source 301 controlled by the radiation source control apparatus 300 are configured to be capable of capturing a radiation image without intervention of the control apparatus 400.

The control apparatus 400 includes an imaging controller 402, an irradiation controller 403, a communication unit 401, the radiation imaging application 404, a display unit 406, an operation UI 407, and a power supply unit 405, and controls the respective components of the radiation imaging system SYS. The imaging controller 402 controls, in accordance with the user setting received via the radiation imaging application 404, the radiation imaging apparatus 100 to control the timing of acquiring image data, set the imaging conditions including the imaging mode for acquiring a radiation image by the detection unit 200, and the like. The irradiation controller 403 controls, in accordance with the user setting received via the radiation imaging application 404, the irradiation condition of radiation applied form the radiation source 301 by controlling the radiation source control apparatus 300. The communication unit 401 controls the communication with the radiation imaging apparatus 100, the radiation source control apparatus 300, and the in-hospital network 600. The radiation imaging application 404 accepts the imaging order and registers the imaging information. The display unit 406 displays a radiation image based on radiation image data acquired by the radiation imaging apparatus 100 or the information of an imaging condition such as the imaging mode for performing imaging. The operation UI 407 can be a mouse or keyboard used to operate the radiation imaging application 404. The power supply unit 405 supplies power to the respective components in the control apparatus 400.

Here, the communication between the control apparatus 400 and the radiation imaging apparatus 100 and the communication between the control apparatus 400 and the radiation source control apparatus 300 may be cable connection communication using a standard such as RS232C, USB, or Ethernet. Further, the communication between the control apparatus 400 and the radiation imaging apparatus 100 and the communication between the control apparatus 400 and the radiation source control apparatus 300 may be communication using a dedicated signal line, or may be wireless communication. Furthermore, the communication between the control apparatus 400 and the radiation imaging apparatus 100 and the communication between the control apparatus 400 and the radiation source control apparatus 300 may be a combination of wired communication and wireless communication.

In the communication between the control apparatus 400 and the radiation imaging apparatus 100, for example, image data and a signal indicating the apparatus status of the radiation imaging apparatus 100 are transmitted from the radiation imaging apparatus 100 to the control apparatus 400. Further, for example, a control signal including a signal indicating the condition setting such as the imaging mode for acquiring image data is transmitted from the control apparatus 400 to the radiation imaging apparatus 100. In the communication between the control apparatus 400 and the radiation source control apparatus 300, for example, a signal indicating the setting of a radiation irradiation condition and the like are transmitted from the control apparatus 400 to the radiation source control apparatus 300. Further, for example, a signal indicating the apparatus status of the radiation source control apparatus 300 and a signal indicating the actual irradiation information at the time of radiation irradiation are transmitted from the radiation source control apparatus 300 to the control apparatus 400.

The image control apparatus 500 performs image processing on the image data transferred from the radiation imaging apparatus 100, and transfers the image data having undergone image processing to the control apparatus 400. A display unit 501, which is used to display a radiation image based on the radiation image data acquired by the radiation imaging apparatus 100 without intervention of the control apparatus 400 when the control apparatus 400 is not operating, is connected to the image control apparatus 500.

Figure 2:
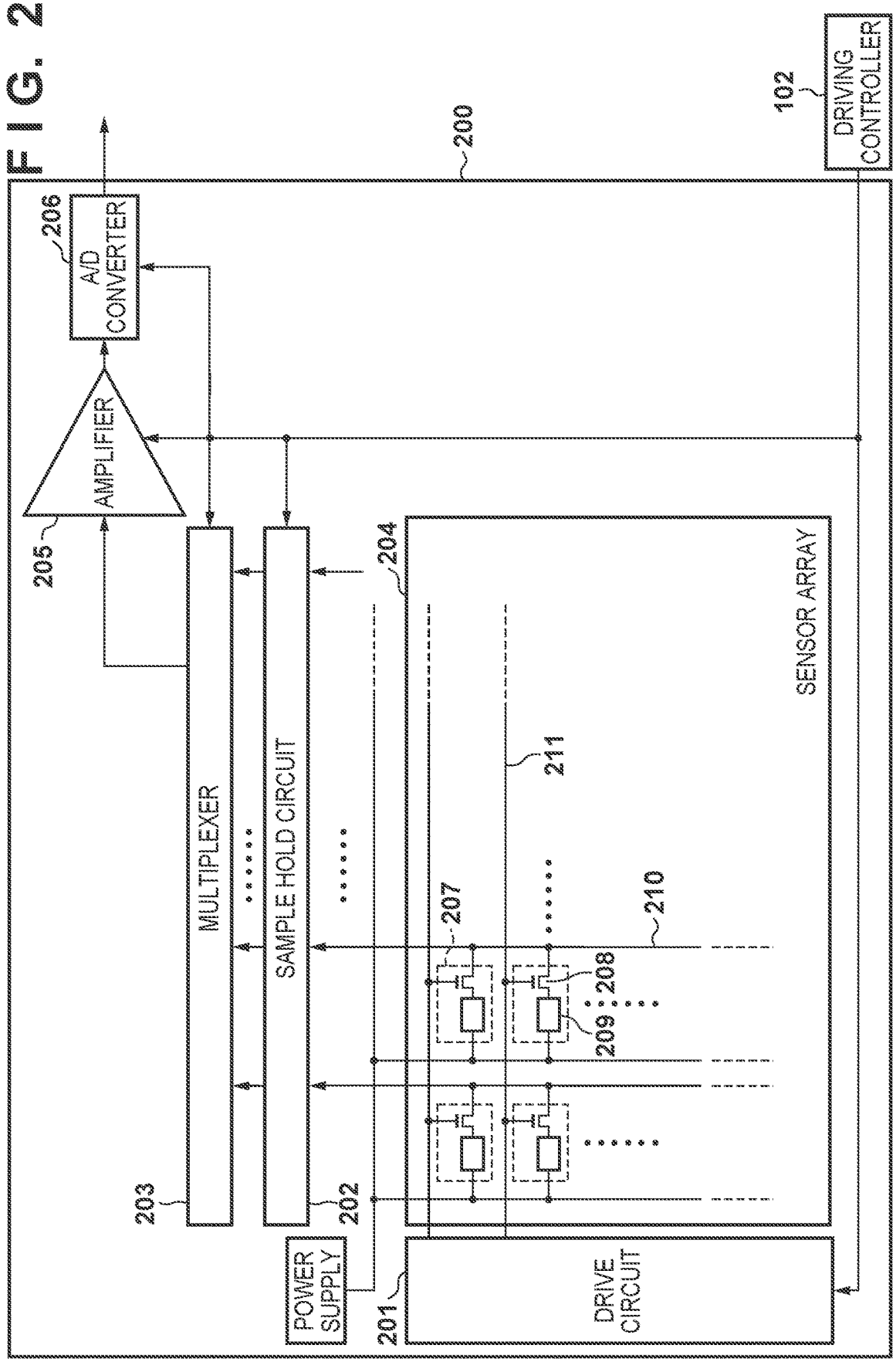
FIG. 2 is a block diagram showing an arrangement example of a detection unit of the radiation imaging apparatus shown in FIG. 1.

FIG. 2 is a block diagram showing an arrangement example of the detection unit 200 of the radiation imaging apparatus 100. The detection unit 200 includes a sensor array 204 including a plurality of pixels 207 arrayed in a two-dimensional array so as to form a plurality of rows and a plurality of columns to acquire a radiation image corresponding to incident radiation. The pixel 207 arranged in the sensor array 204 includes, for example, a switch element 208 such as a TFT (Thin Film Transistor) and a photoelectric conversion element 209, and a scintillator (not shown) can be arranged on the pixel 207 (photoelectric conversion element 209). The scintillator can be integrally formed in the sensor array 204. If the pixel 207 includes the scintillator and the photoelectric conversion element 209, the radiation entering the detection unit 200 is converted into visible light by the scintillator, and electric charges corresponding to the visible light are generated in the photoelectric conversion element 209 where the converted visible light entered. In this manner, a so-called indirect conversion type conversion element which converts the incident radiation into electric charges by the scintillator and the photoelectric conversion element 209 may be used as the pixel 207. Alternatively, for example, a so-called direct conversion type conversion element which is not provided with the scintillator and directly converts the incident radiation into electric charges may be used as the pixel 207. By switching the switch element 208 between the ON (conductive) state and the OFF (non-conductive) state, accumulation of the electric charges generated by the photoelectric conversion element 209 and readout of the electric charges are performed, and image data can be acquired.

In the pixel 207 arranged in the sensor array 204 of the detection unit 200, the switch element 208 is set in the ON state when a voltage for setting the switch element 208 in the ON state is applied for each row from a drive circuit 201 via a common driving line 211. When the switch element 208 is set in the ON state, a signal corresponding to the electric charges accumulated in the pixel 207 is transferred to a sample hold circuit 202 via a signal line 210 connected to each pixel 207. After that, the signals output from the pixels 207 and held in the sample hold circuit 202 are sequentially read out via a multiplexer 203, amplified by an amplifier 205, and converted into digital value image data by an A/D converter 206. When a voltage for setting the switch element 208 in the OFF state is applied from the drive circuit 201 via the driving line 211, the pixel 207 in which readout of the electric charges is completed returns to a state of accumulating electric charges. In this manner, the drive circuit 201 sequentially scans the pixels 207 arranged on the sensor array 204 for each line, and signals finally output from all the pixels 207 are converted into a digital value. With this, the image data for generating a radiation image can be read out. Control for the above-described driving operation, readout operation, or the like of the detection unit 200 is performed by the driving controller 102 of the controller 101. The image data converted into the digital value may be, for example, temporarily stored in the storage unit 109 shown in FIG. 1.

Figure 3:
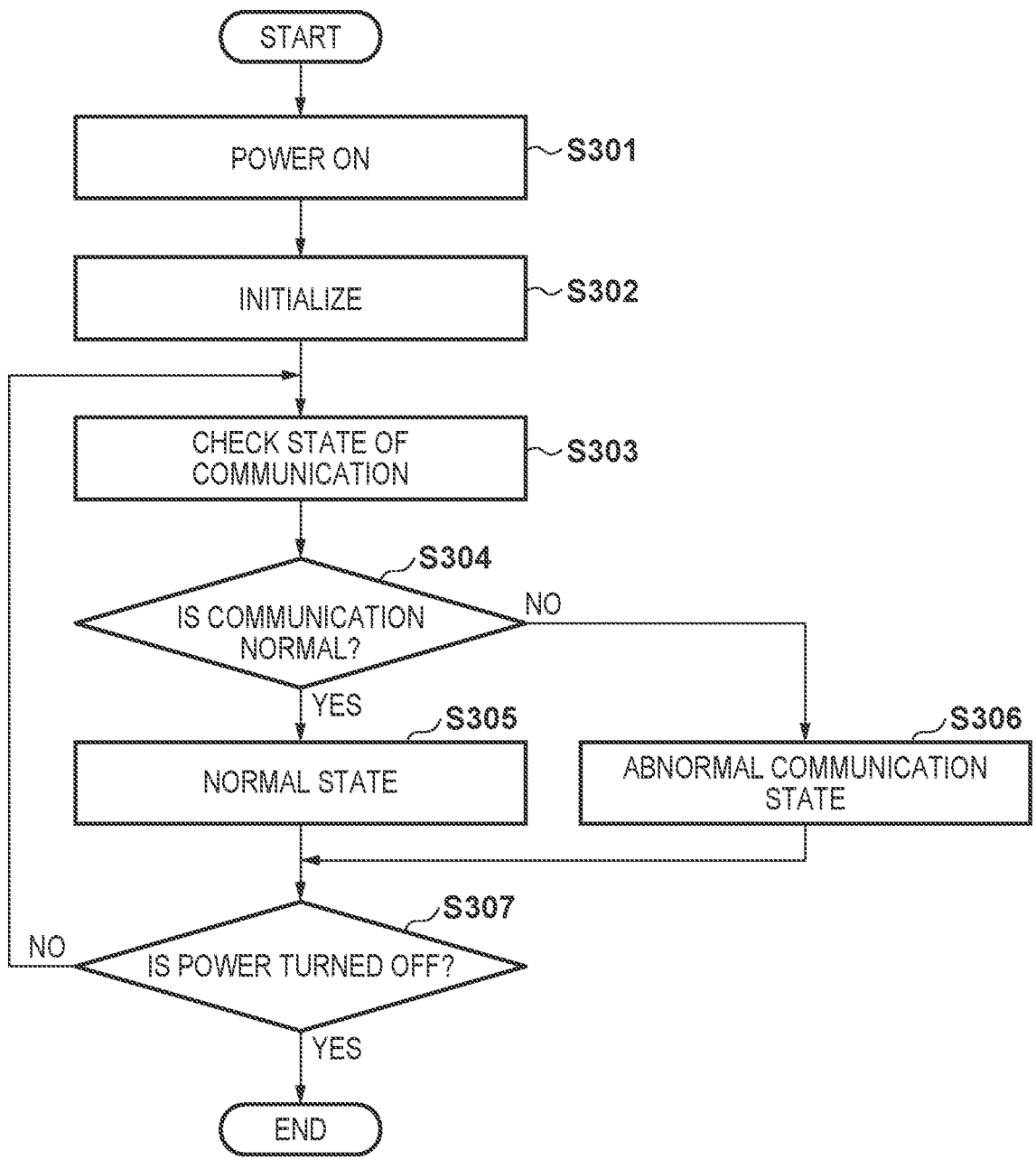
FIG. 3 is a flowchart for explaining an operation of the radiation imaging apparatus shown in FIG. 1.

Next, an operation of the radiation imaging apparatus 100 according to this embodiment will be described. FIG. 3 is a flowchart in which, in the radiation imaging apparatus 100, the controller 101 performs imaging while checking (determining) whether the state of communication with the control apparatus 400 is normal. Here, a case in which the state of communication between the radiation imaging apparatus 100 and the control apparatus 400 is normal is referred to as a normal state, and a case in which the state of communication between the radiation imaging apparatus 100 and the control apparatus 400 is not normal is referred to as an abnormal communication state.

First, in step S301, the radiation imaging apparatus 100 is powered on, and the process transitions to step S302. In step S302, the controller 101 reads out a program stored in the storage unit 109 or the like, and starts control of the respective components of the radiation imaging apparatus 100. In step S302, for example, the setting information, gain correction data, defect correction data, and the like of the radiation imaging apparatus 100 stored in the storage unit 109 are read out, and initialization for imaging preparation is performed. If the initialization is completed, the process transitions to step S303.

In step S303, the controller 101 checks whether the state of communication between the communication unit 112 and the control apparatus 400 is normal. For example, the control apparatus 400 periodically transmits the command to the communication unit 112 of the radiation imaging apparatus 100. The controller 101 checks whether the communication unit 112 receives the periodic command.

Then, in step S304, the controller 101 checks whether the state of communication between the communication unit 112 and the control apparatus 400 is normal. For example, the control apparatus 400 periodically (for example, at intervals of one sec) transmits a command. If the command is received by the communication unit 112, the controller 101 determines that the state of communication is normal. In this case, the state of communication is determined to be the normal state, and the process transitions to step S305. If the communication unit 112 does not receive the command output from the communication apparatus 400 for a certain period (for example, about three secs), the controller 101 determines that the state of communication is not normal, that is, the abnormal communication state. In this case, the state of communication is determined to be the abnormal communication state, and the process transitions to step S306.

In step S305, since the control apparatus 400 operates normally, the communication unit 112 receives, from the control apparatus 400, a control signal including the imaging mode for acquiring a radiation image by the detection unit 200 of the radiation imaging apparatus 100. The imaging mode includes an imaging mode for a fluoroscopic image and an imaging mode for a still image. The control signal further includes a signal for performing the setting corresponding to each imaging mode such as the gain, image size, binning number, frame rate, and the like of the detection unit 200.

If setting of the imaging mode is completed and an imaging instruction such as a press of the exposure switch by the user in the operation UI 302 of the radiation source control apparatus 300 is received, the controller 101 operates the detection unit 200 in the imaging mode corresponding to the control signal. The driving controller 102 performs the radiation image acquiring control 104 and, for example, drives the detection unit 200 in the imaging mode for a fluoroscopic image. Further, the irradiation timing controller 114 outputs, to the radiation source control apparatus 300, a timing signal indicating the radiation irradiation timing. In accordance with the timing signal, the radiation source control apparatus 300 causes the radiation source 301 to apply radiation. The radiation image data acquired by the radiation imaging apparatus 100 is transferred to the image control apparatus 500. The radiation image data transferred to the image control apparatus 500 undergoes image processing or the like in the image control apparatus 500, and is transferred to the control apparatus 400. Thus, a fluoroscopic image based on the acquired radiation image data is displayed on the display unit 406.

On the other hand, if it is determined in step S304 that the state of communication is the abnormal communication state, the communication unit 112 cannot receive the control signal for setting the imaging mode from the control apparatus 400 in step S306. Therefore, if an imaging instruction such as a press of the exposure switch in the operation UI 302 is received, the controller 101 operates the detection unit 200 in the abnormal imaging mode set in advance. For example, respective conditions including "for a fluoroscopic image", the high sensitivity, the maximum image size, and a frame rate of 15 fps are set as the abnormal imaging mode.

If the exposure switch is pressed in the operation UI 302 of the radiation source control apparatus 300, the driving controller 102 performs the radiation image acquiring control 104, and drives the detection unit 200 in the abnormal imaging mode. Further, the irradiation timing controller 114 outputs, to the radiation source control apparatus 300, a timing signal indicating the radiation irradiation timing. In accordance with the timing signal, the radiation source control apparatus 300 causes the radiation source 301 to apply radiation. The radiation image data acquired by the radiation imaging apparatus 100 is transferred to the image control apparatus 500. The radiation image data transferred to the image control apparatus 500 undergoes image processing or the like in the image control apparatus 500. A fluoroscopic image based on the acquired radiation image data is displayed on the display unit 501.

In this case, the radiation imaging apparatus 100 may output a notification signal indicating that it is in the abnormal communication state to the display unit 501 via the image control apparatus 500. The display unit 501 notifies the user that the radiation imaging apparatus 100 is operating in the abnormal communication state. For example, the notification signal may be attached to the header information of the radiation image data or the like. Based on the header information, the image control apparatus 500 may determine whether to display a fluoroscopic image on the display unit 501, or determine whether to transfer the radiation image data to the control apparatus 400. Further, for example, when the radiation image is always displayed on the display unit 406 in the normal state, the user can determine that the radiation imaging apparatus 100 is operating in the abnormal communication state if the radiation image is not displayed on the display unit 406.

When the state of communication has changed between the normal state and the abnormal communication state, the controller 101 may transition from the normal state to the abnormal communication state or from the abnormal communication state to the normal state. For example, after capturing of a fluoroscopic image or a still image is completed, the process transitions to step S307 and, if the power is not turned off by the user, the controller 101 may transition to step S303 and check the state of communication. Further, the controller 101 may check the state of communication also during capturing of a fluoroscopic image or a still image. When the state of communication has changed between the normal state and the abnormal communication state during acquisition of radiation image data, the controller 101 may interrupt the operation of acquiring the radiation image data whose capturing is in progress, and transition from the normal state to the abnormal communication state or from the abnormal communication state to the normal state. Alternatively, when the state of communication has changed between the normal state and the abnormal communication state during acquisition of radiation image data, the controller 101 may transition from the normal state to the abnormal communication state or from the abnormal communication state to the normal state after the radiation image data whose capturing is in progress is acquired. With this, it is possible to hold the radiation image data whose capturing has already started.

After the radiation image is captured, if the radiation imaging apparatus 100 is powered off by the user, the sequence of imaging for a radiation image described above is terminated.

Here, the offset amount regarding the offset component included in the radiation image data changes in accordance with the imaging conditions for capturing the radiation image. Further, the offset amount regarding the offset component changes in accordance with a temperature change occurring along with an operation of the radiation imaging apparatus or the like. Accordingly, it is required to reacquire an offset image corresponding to each imaging mode at an appropriate timing. If the state of communication between the radiation imaging apparatus 100 and the control apparatus 400 is the normal state, the control apparatus 400 appropriately operates the radiation imaging apparatus 100 so as to acquire the offset image data corresponding to each imaging mode while radiation irradiation is not performed.

On the other hand, if the state of communication between the radiation imaging apparatus 100 and the control apparatus 400 is the abnormal communication state, the control signal cannot be received from the control apparatus 400. For example, if the control apparatus 400 is down due to some reason, the abnormal communication state can occur. When the state of communication with the control apparatus 400 is restored and the user sets an appropriate imaging mode to perform imaging, if a certain time has elapsed since the last offset image data was acquired, it is required to reacquire offset image data. In this case, it may take a long time until reacquisition of the offset image data is completed and imaging is started. Therefore, in this embodiment, in the abnormal communication state, the controller 101 of the radiation imaging apparatus 100 operates the detection unit 200 so as to acquire the offset image data for an imaging mode different from the above-described abnormal imaging mode while radiation irradiation is not performed. The acquired offset image data is stored in the storage unit 109. With this, when the control apparatus 400 is restored from the down state, it is possible to quickly start the imaging operation for acquiring a radiation image. Thus, the convenient radiation imaging apparatus 100 and radiation imaging system SYS can be implemented.

FIG. 4 is a flowchart illustrating processing of updating offset image data. Here, a case will be described in which the offset controller 108 updates the offset image data in the steps to be described below. However, the present invention is not limited to this, and it is only required that the offset image data is acquired by appropriate cooperation of the respective components of the radiation imaging apparatus 100. Since the offset controller 108 is included in the controller 101 as shown in FIG. 1, the offset controller 108 may be simply described as the controller 101 below.

First, in step S401, the timer 113 measures the time elapsed since the offset image data was acquired. If the offset image data has never been acquired, the elapsed time is set to a maximum time.

Then, in step S402, the controller 101 (offset controller 108) determines whether a predetermined time has elapsed since the last offset image data was acquired. If the elapsed time measured by the timer 113 exceeds a time T (elapsed time>T), the process transitions to step S403. If the elapsed time is equal to or shorter than the time T (elapsed time≤T), the process returns to step S401. For example, the time T may be five min.

In step S403, the controller 101 determines whether imaging is in progress. That is, the controller 101 checks whether radiation irradiation is performed. If radiation irradiation is not performed, the process transitions to step S404. On the other hand, if radiation irradiation is performed and capturing of a radiation image is in progress, the process returns to step S401. If imaging is not in progress, the driving controller 102 is performing the imaging preparation driving control 103.

Then, in step S404, the driving controller 102 switches driving from the imaging preparation driving control 103 to the offset image acquiring control 105, and updates the offset image data. With this, the controller 101 operates the detection unit 200 so as to acquire the offset image data at a timing at which the predetermined time has elapsed since the last offset image data was acquired and radiation irradiation is not performed.

In the normal state, while radiation irradiation is not performed, the controller 101 operates, for example, under the control of the control apparatus 400, the detection unit 200 so as to acquire the offset image data for all the imaging modes set in the radiation imaging apparatus 100. With this, the offset image data for all the imaging modes including the imaging mode for a fluoroscopic image and the imaging mode for a still image are sequentially updated.

On the other hand, in the abnormal communication state in which the control signal cannot be received from the control apparatus 400, the controller 101 drives the detection unit 200 such that it acquires the radiation image data only in the abnormal imaging mode. However, as for acquisition of the offset image data, the detection unit 200 is operated so as to acquire the offset image data for the imaging mode different from the abnormal imaging mode. For example, in the abnormal communication state, the controller 101 may operate the detection unit to acquire the offset image data for all the imaging modes set in the radiation imaging apparatus 100 while radiation irradiation is not performed. If update of the offset image data is completed, the timer 113 resets the elapsed time to 0.

Update of the offset image data is not limited to be performed for all the imaging modes. For example, in the abnormal communication state, the controller 101 may operate the detection unit 200 so as to acquire the offset image data for at least two imaging modes including the abnormal imaging mode while radiation irradiation is not performed. In this case, for example, the offset image data for one or more imaging modes frequently used for imaging may be acquired separately from the offset image data for the abnormal imaging mode. The imaging mode for which the offset image data is acquired may be set at the time of shipping from the factory, or may be set appropriately by the user. Further, the storage unit 109 may store the imaging mode having high frequency of use, and the offset image data for one or more stored imaging modes having high frequency of use may be acquired. In the abnormal communication state, at least one offset image data for the imaging mode different from the abnormal imaging mode is acquired. With this, comparing to a case in which no offset image data is acquired, it is possible to shorten the time for waiting reacquisition of the offset image data when the communication state has returned to normal.

As has been described above, even when the state of communication between the radiation imaging apparatus 100 and the control apparatus 400 is not normal, the offset image data is updated. Thus, even when the state of communication between the radiation imaging apparatus 100 and the control apparatus 400 has changed from the normal state to the abnormal communication state due to a communication error or when the state of communication has returned to normal and changed from the abnormal communication state to the normal state, the offset image data has been updated. Accordingly, it is possible to immediately capture a fluoroscopic image or a still image. Therefore, the waiting time is suppressed, and the convenient radiation imaging apparatus 100 and radiation imaging system SYS can be implemented.

Although not included in the steps for acquiring the offset image data illustrated in FIG. 4, if the offset image data is acquired immediately after capturing a radiation image, an afterimage may be included in the offset image data. In order to suppress the influence of the afterimage, the timer 113 further measures the time elapsed since the radiation image data was acquired. The controller 101 may operate the detection unit 200 so as to acquire the offset image data at a timing at which a predetermined time has elapsed since the last offset image data was acquired, radiation irradiation is not performed, and a predetermined time has elapsed since the last radiation image data was acquired.

Other Embodiments

Embodiment(s) of the present invention can also be realized by a computer of a system or apparatus that reads out and executes computer executable instructions (e.g., one or more programs) recorded on a storage medium (which may also be referred to more fully as 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-021062, filed Feb. 12, 2021, which is hereby incorporated by reference herein in its entirety.

What is claimed is:

1. A radiation imaging apparatus, comprising:
a detection unit comprising a plurality of pixels configured to acquire a radiation image corresponding to incident radiation;
a communication unit configured to receive from a control apparatus a control signal including an imaging mode for acquiring the radiation image; and
a controller configured to:
operate the detection unit in an imaging mode corresponding to the control signal if an imaging instruction is received in a first state in which a state of communication between the communication unit and the control apparatus is normal;
operate the detection unit in an abnormal imaging mode set in advance if the imaging instruction is received in a second state in which the state of communication is not normal;

operate the detection unit so as to acquire offset image data for an imaging mode different from the abnormal imaging mode while radiation irradiation is not performed in the second state; and operate the detection unit so as to acquire offset image data at a timing at which a predetermined time has elapsed since last offset image data was acquired and radiation irradiation is not performed, wherein the controller includes a timer configured to measure a time elapsed since the offset image data was acquired.

2. The apparatus according to claim 1, wherein the controller is configured to operate the detection unit so as to acquire offset image data for at least two imaging modes including the abnormal imaging mode while radiation irradiation is not performed in the second state.

3. The apparatus according to claim 1, wherein the controller is configured to operate the detection unit so as to acquire offset image data for all imaging modes set in the radiation imaging apparatus while radiation irradiation is not performed in the second state.

4. The apparatus according to claim 1, wherein the timer is configured to measure a time elapsed since radiation image data was acquired, and the controller is configured to operate the detection unit so as to acquire offset image data at a timing at which a predetermined time has elapsed since the last offset image data was acquired, radiation irradiation is not performed, and a predetermined time has elapsed since last radiation image data was acquired.

5. The apparatus according to claim 1, wherein the controller is configured to transition from the first state to the second state or from the second state to the first state after the radiation image data is acquired when the state of communication has changed between the first state and the second state during acquisition of radiation image data.

6. The apparatus according to claim 1, wherein the controller is configured to interrupt an operation of acquiring the radiation image data and transitions from the first state to the second state or from the second state to the first state when the state of communication has changed between the first state and the second state during acquisition of radiation image data.

7. A radiation imaging system, comprising:
the radiation imaging apparatus according to claim 1; and
a control apparatus configured to communicate the control signal to the radiation imaging apparatus.

8. The system according to claim 7, wherein the control apparatus is configured to periodically transmit a command to a communication unit, and the controller is configured to determine whether the state of communication is normal by determining whether the communication unit receives the command.

9. The system according to claim 7, further comprising a display unit configured to display a radiation image based on radiation image data acquired by the radiation imaging apparatus without intervention of the control apparatus.

10. The system according to claim 9, wherein the radiation imaging apparatus is configured to output to the display unit a notification signal indicating that the radiation imaging apparatus is in the second state, and the display unit is configured to notify that the radiation imaging apparatus is in the second state.

11. The system according to claim 10, wherein the notification signal is attached to radiation image data.

12. A control method of a radiation imaging apparatus that comprises a detection unit in which a plurality of pixels used to acquire a radiation image corresponding to incident radiation are arranged, a timer, and a communication unit configured to communicate, with a control apparatus, a control signal including an imaging mode of acquiring the radiation image by the detection unit, the method comprising the steps of:

determining whether a state of communication between the communication unit and the control apparatus is normal;

operating the detection unit in an imaging mode corresponding to the control signal if an imaging instruction is received in a first state in which the state of communication is normal; and operating the detection unit in an abnormal imaging mode set in advance if an imaging instruction is received in a second state in which the state of communication is not normal, wherein the detection unit is operated so as to acquire offset image data for an imaging mode different from the abnormal imaging mode while radiation irradiation is not performed in the second state, the detection unit is operated so as to acquire offset image data at a timing at which a predetermined time has elapsed since last offset image data was acquired and radiation irradiation is not performed, and the timer measures a time elapsed since the offset image data was acquired.

13. A non-transitory computer-readable storage medium storing a program for causing a computer to execute a control method of a radiation imaging apparatus that comprises a detection unit in which a plurality of pixels used to acquire a radiation image corresponding to incident radiation are arranged, a timer, and a communication unit configured to communicate, with a control apparatus, a control signal including an imaging mode of acquiring the radiation image by the detection unit, the method comprising the steps of:

determining whether a state of communication between the communication unit and the control apparatus is normal;

operating the detection unit in an imaging mode corresponding to the control signal if an imaging instruction is received in a first state in which the state of communication is normal; and operating the detection unit in an abnormal imaging mode set in advance if an imaging instruction is received in a second state in which the state of communication is not normal, wherein the detection unit is operated so as to acquire offset image data for an imaging mode different from the abnormal imaging mode while radiation irradiation is not performed in the second state, wherein the detection unit is operated so as to acquire offset image data at a timing at which a predetermined time has elapsed since last offset image data was acquired and radiation irradiation is not performed, and the timer measures a time elapsed since the offset image data was acquired.

14. A radiation imaging system comprising a radiation imaging apparatus, a control apparatus and a display unit, the radiation imaging apparatus comprising:

a detection unit comprising a plurality of pixels configured to acquire a radiation image corresponding to incident radiation;

a communication unit configured to receive from a control apparatus a control signal including an imaging mode for acquiring the radiation image; and a controller configured to:
operate the detection unit in an imaging mode corresponding to the control signal if an imaging instruction is received in a first state in which a state of communication between the communication unit and the control apparatus is normal;
operate the detection unit in an abnormal imaging mode set in advance if the imaging instruction is received in a second state in which the state of communication is not normal; and
operate the detection unit so as to acquire offset image data for an imaging mode different from the abnormal imaging mode while radiation irradiation is not performed in the second state, wherein
the radiation imaging apparatus outputs to the display unit a notification signal indicating that the radiation imaging apparatus is in the second state, and
the display unit is configured to notify that the radiation imaging apparatus is in the second state,
the display unit is configured to display a radiation image based on radiation image data acquired by the radiation imaging apparatus without intervention of the control apparatus, and
the control apparatus is configured to communicate the control signal to the radiation imaging apparatus.

15. The system according to claim 14, wherein the notification signal is attached to radiation image data.

* * * * *